United States Patent [19]

Borchers et al.

[11] Patent Number: 5,371,246

[45] Date of Patent: Dec. 6, 1994

[54] PREPARATION OF TETRAHYDROPYRAN-4-CARBOXYLIC ACID AND ESTERS THEREOF

[75] Inventors: Dirk Borchers, Birkenheide; Rolf Fischer, Heidelberg; Norbert Goetz, Worms; Thomas Kuekenhoehner, Boehl-Iggelheim; Werner Schnurr, Herxheim, all of Germany

[73] Assignee: BASF Aktiengesellschaft, Ludwigshafen, Germany

[21] Appl. No.: 110,219

[22] Filed: Aug. 23, 1993

[30] Foreign Application Priority Data

Aug. 28, 1992 [DE] Germany .............. 4228669

[51] Int. Cl.⁵ .................................. C07D 309/06
[52] U.S. Cl. ........................................... 549/425
[58] Field of Search ................................ 549/425

[56] References Cited

U.S. PATENT DOCUMENTS 4,837,346  6/1989  Becker et al. .................. 549/425

FOREIGN PATENT DOCUMENTS 284969  3/1983  European Pat. Off. .

*Primary Examiner*—Nicky Chan
*Attorney, Agent, or Firm*—Keil & Weinkauf

[57] ABSTRACT

A process for the preparation of tetrahydropyran-4-carboxylic acid and esters thereof of the general formula I

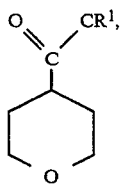
(I)

in which
$R^1$ denotes hydrogen, $C_1$-$C_6$ alkyl, $C_5$-$C_8$ cycloalkyl, or aryl by the reaction of a dihydro-2(3H)furanone of the general formula II

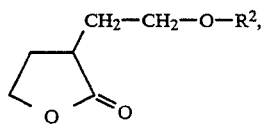
(II)

in which
$R^2$ denotes hydrogen, $C_1$-$C_6$ alkyl, or —CO—$R^3$ and
$R^3$ denotes hydrogen or $C_1$-$C_6$ alkyl, with water or an alcohol of the general formula III $$R^1\text{—OH} \qquad \text{(III)},$$

in which
$R^1$ has the aforementioned meaning,
at temperatures ranging from 200° to 350° C. in the presence of a heterogenous acid catalyst, in which use is made of a fixed heterogenous acid catalyst.

6 Claims, No Drawings

PREPARATION OF TETRAHYDROPYRAN-4-CARBOXYLIC ACID AND ESTERS THEREOF

The present invention relates to an improved process for the preparation of tetrahydropyran-4-carboxylic acid and esters thereof, in which 3-(2'-hydroxyethyl)-dihydro-2(3H)furanone or its esters or ethers are caused to react with alcohols and/or water in the presence of acidic fixed bed catalysts.

EP-A 284,969 discloses that it is possible to prepare tetrahydropyran-4-carboxylates by the reaction of 3-(2'-hydroxyethyl)-dihydro-2(3H)furanone or esters or ethers thereof with alcohols in the presence of acid-acting catalysts. The reaction can be carried out batchwise or continuously as a fixed bed reaction using fixed bed catalysts, e.g., by methods involving packed bubble columns or trickle-bed columns in the liquid or gaseous phase, e.g., in a fluidized bed or alternatively with fixed catalysts suspended in the liquid phase. Another alternative is to use acid catalysts which are homogeneously dissolved in the liquid phase.

The patent examples demonstrate that when operating in the gas phase in the presence of fluidized $Al_2O_3$ catalysts at a temperature of from 240° to 270° C. yields of tetrahydropyrancarboxylate of only 36 to 42% are achieved (based on 3-(2'-hydroethyl)-dihydro-2(3H)furanone used)(Examples 1 and 2). The by-products formed under these conditions comprise from 18 to 20 % of 3-(2'-methoxyethyl)-dihydro-2(3H)furanone and from 16 to 27% of 3-vinyldihydro-2(3H)furanone. Example 1b demonstrates that the by-product 3-(2'-methoxyethyl)-dihydro-2(3H)furanone can be reacted with methanol to form methyl tetrahydropyran-4-carboxylate to give a yield of 26%. On the other hand, the reaction of the by-product 3-vinyldihydro-2(3H)furanone with methanol as described in Example 1c provides a yield of only 10%.

It is thus an object of the present invention to overcome the aforementioned drawbacks and to increase the yield of tetrahydropyrancarboxylate.

Accordingly, we have found a novel and improved process for the preparation of tetrahydropyran-4-carboxylic acid and esters thereof of the general formula I

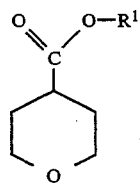
(I)

in which
$R^1$ denotes hydrogen, $C_1$–$C_6$ alkyl, $C_5$–$C_8$ cycloalkyl, or aryl by the reaction of a dihydro-2(3H)furanone of the general formula II

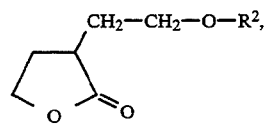
(II)

in which $R^2$ denotes hydrogen, $C_1$–$C_6$ alkyl, or —CO—$R^3$ and
$R^3$ denotes hydrogen or $C_1$–$C_6$ alkyl, with water or an alcohol of the general formula III $$R^1\text{—OH} \quad (III),$$

in which
$R^1$ has the aforementioned meaning,
at temperatures ranging from 200° to 350° C. in the presence of a heterogenous acid catalyst, wherein use is made of a fixed heterogenous acid catalyst.

The process of the invention can be carried out as follows:

The reaction of dihydro-2(3H)furanones II with alcohols III can be carried out in the gas phase or in the liquid phase over fixed heterogenous acid catalysts at temperatures ranging from 200° to 350° C. and preferably from 200° to 300° C. and more preferably from 230° to 270° C. and pressures of from 0.01 to 100 bar and preferably from 0.1 to 5 bar and more preferably from 0.5 to 2 bar, in particular under standard pressure (atmospheric pressure). It is general to operate using throughputs of from 0.1 to 10 g and especially of from 0.1 to 5 g of tetrahydrofuranone II per gram of catalyst per hour.

The molar ratio of alcohol III to the dihydro-2(3H)furanone II is advantageously from 0.5:1 to 10:1 and preferably from 1:1 to 5:1.

It may be advantageous to add water to the mixture of dihydro-2(3H)furanone II and alcohol III. The amount of water present may be from 0.01 to 5 mol and preferably from 0.5 to 2 mol per mole of dihydro-2(3H)furanone II.

The mixture of dihydro-2(3H)furanone, alcohol, and, optionally, water can be preevaporated in a separate evaporator and then passed to the catalyst bed. An alternative possibility is to evaporate the mixture in the reactor itself, e.g., in a layer of inert packing material heated to the required temperature and situated upstream of the catalyst bed.

The preparation of tetrahydropyran-4-carboxylates I may be effected, for example, by evaporating a mixture of the dihydro-2(3H)furanone II and the respective alcohol III and then passing the vapors, optionally together with an inert gas such as nitrogen, carbon dioxide or argon, over a fixed catalyst at the desired reaction temperature. The effluent can be condensed by means of suitable cooling equipment and subsequently purified by fractional distillation. Unconverted 3-(2'-hydroethyl)-dihydro-2(3H)furanone or ethers or esters thereof can be recycled to the reaction.

Suitable fixed heterogeneous catalysts are fixed bed catalysts, e.g., acid-acting oxides of Group IIIa, Group IVa, Group IVb, Group Vb, and Group VIb elements as listed in the Periodic Table. For example, mention may be made of heterogeneous acid catalysts such as silicon dioxide in the form of silica gel, kieselguhr, quartz, and also titanium dioxide, zirconium dioxide, phosphorus pentoxide, vanadium pentoxide, boron trioxide, aluminum oxide, chromium oxides, molybdenum oxides, tungsten oxides or mixtures thereof. Zeolites are also suitable, e.g., Y-type zeolites. A particularly preferred catalyst is aluminum oxide.

3-(2'-Hydroxyethyl)-dihydro-2( 3H)furanone can be prepared, e.g., by the reaction of ethyl acetoacetate with ethylene oxide (EP-A 246,581).

The substituents $R^1$, $R^2$, and $R^3$ in the compounds I, II, and III have the following meanings:

$R^1$, $R^2$, and $R^3$ independently denote hydrogen, $C_1$–$C_6$ alkyl and preferably $C_1$–$C_4$ alkyl such as methyl, ethyl, n-propyl, isopropyl, n-butyl, isobutyl, sec-butyl, and tert-butyl and more preferably methyl and ethyl, $R1$ $R^1$ additionally denotes $C_5$–$C_8$ cycloalkyl such as cyclopentyl, cyclohexyl, cycloheptyl, and cyclooctyl and preferably cyclopentyl, cyclohexyl, and cyclooctyl and more preferably cyclopentyl and cyclohexyl, aryl such as phenyl, 1-naphthyl, 2-naphthyl, 1-anthryl, 2-anthryl, and 9-anthryl and preferably phenyl, 1-naphthyl, and 2-naphthyl and more preferably phenyl, and $R^2$ additionally denotes —CO—$R^3$.

Suitable dihydro-2(3H)furanones II are, e.g., 3-(2'-hydroxyethyl)-dihydro-2(3H)furanone, whose hydroxyethyl group can be etherified to give the, say, methyl, ethyl, propyl, or butyl ether or can be esterified, e.g., with formic acid, acetic acid, propionic acid, butyric acid, n-valeric acid, isovaleric acid, or benzoic acid. Particularly preferred starting compounds II are the esters of 3-(2'-hydroxyethyl)-dihydro-2(3H)furanone with acetic acid and propionic acid. Suitable alcohols of the formula III are, for example, methanol, ethanol, n-propanol, isopropanol, tert-butanol, n-butanol, isobutanol, sec-butanol, n-pentanol, n-hexanol, phenol, cyclo-pentanol, and cyclohexanol, Methanol, ethanol and propanols are particularly suitable.

Using the process of the invention the yield of tetrahydropyran-4-carboxylate I can be increase by roughly 20% as compared with EP-A-1 284,969. Moreover, the concentration of 5-oxaspiro[2.4]heptan-4-one, 3-ethylidenedihydro-2(3H)furanone and 3-vinyldihydro-2(3H)furanone is reduced.

It is surprising to observe that the change from fluid bed to fixed bed operation not only increases the yield of tetrahydropyran-4-carboxylate but also considerably raises the ratio of 3-(2'-alkoxyethyl)-dihydro-2(3H)furanone to 5-oxaspiro-[2.4]heptan-4-one/3-vinyldihydro-2(3H)furanone.

The tetrahydropyran-4-carboxylates I which can be produced by the process of the invention are valuable intermediates, which can be processed, e.g., to the desired tetrahydropyran-4-carbaldehyde (DE-A 3,121,355, DE-A 3,314,816, DE-A 3,340,265, DE-A 3,821,197 and DE-A 4,039,918).

EXAMPLES

Example 1

A solution consisting of 57 wt % of 3-(2'-acetoxyethyl)-dihydro-2(3H)furanone and 43wt % of methanol was pumped into an evaporator (300° C.) at a rate of 170 g per hour, whence the vapors were passed together with 80 L/h of nitrogen over 560 g (950 mL) of $Al_2O_3$ (1.3 mm extrudates) at a reactor temperature of 250° C. using a trickle-bed method. The gaseous effluent was condensed in cold traps and analyzed by gas chromatography. 61 mol % of methyl tetrahydropyran-4-carboxylate was formed, plus 26 mol % of 3-(2'-methoxyethyl)-dihydro-2(3H)furanone and 5 mol % of 5-oxaspiro[2.4]heptan-4-one. The conversion of 3-(2'-acetoxyethyl)-dihydro-2(3H)furanone was 97%.

Example 2

A solution consisting of 53 wt % of 3-(2'-acetoxyethyl)-dihydro-2(3H)furanone, 39 wt % of methanol, and 8 wt % of water was evaporated at a rate 25 g per hour and the vapors were passed at a temperature of 250° C. over 90 g of aluminum oxide catalyst (diameter 1.5 mm) in a tubular reactor. The gaseous effluent was condensed in cold traps and analyzed by gas chromatography. The experiment was carried out for a period of 12 h and the total amount of starting material used was 600 g. 62 mol % of methyl tetrahydropyran-4-carboxylate was formed, plus 20 mol % of 3-(2'-methoxyethyl)-dihydro-2(3H)furanone and 3 mol % of 5-oxaspiro-[2.4]heptan-4-one. The conversion of 3-(2'-acetoxyethyl)-dihydro-2(3H)furanone was better than 99%.

Example 3

A solution consisting of 45 wt % of 3-(2'-hydroxyethyl)-dihydro-2(3H)furanone, 45 wt % of methanol, and 10 wt % of water, was evaporated at a rate of 25 g per hour and the vapors were passed over 90 g of aluminum oxide catalyst (diameter 1.5 ram) in a tubular reactor at a temperature of 250° C. The gaseous effluent was condensed in cold traps and analyzed by gas chromatography. The experiment was carried out for a period of 60 h and the total amount of starting material used was 1500 g. 57 mol % of methyl tetrahydropyran-4-carboxylate was formed, plus 32 mol % of 3-(2'-methoxyethyl)-dihydro-2(3H)furanone and 4 mol % of 5-oxaspiro-[2.4]heptan-2-one, the conversion of 3-(2'-hydroxyethyl)-dihydro-2(3H)furanone being better than 97%.

Example 4

During an experimental period of 36 h a total of 900 g of a solution consisting of 53 wt % of 3-(2'-methoxyethyl)-dihydro-2(3H)furanone and 47 wt % of methanol was evaporated and the vapors were passed over 90 g of aluminum oxide catalyst (diameter 1.5 ram) at a temperature of 250° C. in a tubular reactor. Following condensation of the gaseous effluent, analysis was effected using gas chromatography. The conversion of 3-(2'-methoxyethyl)-dihydro-2(3H)furanone was 53%. 46 mol % of methyl tetrahydropyran-4-carboxylate and 7 mol % of 5-oxaspiro-[2.4]heptan-2-one were formed.

Example 5

In a cyclindrical reaction tube having a capacity of 250 mL there were packed $Al_2O_3$-extrudates (1.5 mm in diameter, 3 mm in length). The reaction temperature having been set to 250° C., there were passed through said reactor over said catalyst 20 g/h of a mixture consisting of 65 wt % of 3-(2'-hydroxyethyl)-dihydro-2(3H)furanone and 35 wt% of water. Concurrently, 200 L of nitrogen were passed through the reaction tube under standard pressure in parallel flow. The experiment was carried out over a period of 8 h. In all 158 g of reaction product were formed. At the commencement of distillation the water present in excess was removed.

The subsequently isolated crude product contained 28.0 wt % of 3-(2'-hydroxyethyl)-dihydro-2(3H)furanone (starting product)

17.4 wt % of tetrahydropyran-4-carboxylic acid and 29.1 wt % of [2-(dihydro-2(3H)furanon-3-yl)-ethyl] tetrahydropyran-4-carboxylate, this giving, at a conversion rate of 72%, a selectivity toward tetrahydropyran-4carboxylic acid of 24%. The selectivity toward the ester was 40%.

Example 6

In a cylindrical reaction tube having a capacity of 250 mL there were packed Al₂O₃ -extrudates (1.5 mm in diameter, 3 mm in length). The reaction temperature having been set to 250° C. and the pressure to 500 mbar, 30 g/h of a mixture of 57 wt % of 3-(2'-acetoxyethyl)-dihydro-2(3H)furanone and 43 wt % of methanol were passed over this catalyst. The gaseous reaction product was condensed in cold traps and its composition analyzed by gas chromatography. Under these reaction conditions, 59 mol % of methyl tetrahydropyran-4-carboxylate was formed, plus 18 mol % of 3-( 2'-methoxyethyl)-dihydro-2(3H)furanone and 5 mol % of 5- oxaspiro[2.4 ]heptan-2-one. The conversion of 3-(2'-acetoxyethyl)-dihydro-2(3H)furanone was better than 95%.

Example 7

A solution consisting of 37 wt % of 3-(2'-acetoxyethyl)-dihydro-2(3H)furanone, 19 wt % of 3-(2'-methoxyethyl)dihydro-2(3H)furanone, and 44 wt % of methanol, was passed over 140 g of aluminum oxide catalyst (1.5 mm extrudates) in a tubular reactor at a rate of 38 g per hour with the addition of 10 Lh of nitrogen, at a temperature of 250° C. The gaseous effluent was condensed in cold traps and analyzed by gas chromatography. 53 mol % of methyl tetrahydropyran-4-carboxylate was formed, plus 41 mol % of 3-(2'-methoxyethyl)-dihydro-2(3H)furanone and 3 mol % of 5-oxaspiro[2.4 ]heptan-2-one. The conversion of 3-( 2'-acetoxyethyl)-dihydro-2( 3H)furanone was better than 99%.

We claim:

1. A process for the preparation of tetrahydropyran-4-carboxylic acid and esters thereof of the general formula I

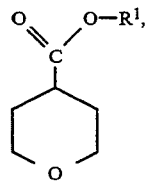
(I)

in which $R^1$ denotes hydrogen, $C_1$–$C_6$ alkyl, $C_5$–$C_8$ cycloalkyl, or aryl by the reaction of a dihydro-2(3H)furanone of the general formula II

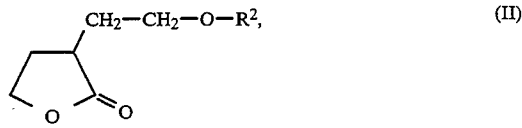
(II)

in which $R^2$ denotes hydrogen, $C_1$–$C_6$ alkyl, or —CO—$R^3$ and $R^3$ denotes hydrogen or $C_1$–$C_6$ alkyl, with water or an alcohol of the general formula III

(III), in which $R^1$ has the aforementioned meaning, at temperatures ranging from 200° to 350° C. in the presence of a heterogenous acid catalyst, wherein use is made of a fixed heterogenous acid catalyst.

2. A process for the preparation of tetrahydropyran-4-carboxylic acid and esters thereof as claimed in claim 1, wherein the reaction is carried out at a temperature of from 200° to 300° C.

3. A process for the preparation of tetrahydropyran-4-carboxylic acid and esters thereof as claimed in claim 1, wherein the reaction is carried out at a temperature of from 230° to 270° C.

4. A process for the preparation of tetrahydropyran-4-carboxylic acid and esters thereof as claimed in claim 1, wherein the acid heterogenous catalyst used is a member selected from the group consisting of an acid-acting oxide of a Group IIIa, Group IVa, Group IVb, Group Vb, and Group VIb element.

5. A process for the preparation of tetrahydropyran-4-carboxylic acid and esters thereof as claimed in claim 1, wherein the acidic heterogenous catalyst used is aluminum oxide.

6. A process for the preparation of tetrahydropyran-4-carboxylic acid and esters thereof as claimed in claim 1, wherein the butyrolactone II used is a member selected from the group consisting of 3-(2'-acetoxyethyl)-dihydro-2(3H)furanone, 3-(2'-hydroxyethyl)-dihydro-2(3H)furanone and 3-(2'-methoxyethyl)-dihydro-2(3H)furanone.

* * * * *